United States Patent [19]
Bret et al.

[11] Patent Number: 6,146,648
[45] Date of Patent: Nov. 14, 2000

[54] SOFTENING LOTION COMPOSITION, USE THEREOF IN PAPER MAKING, AND RESULTING PAPER PRODUCT

[75] Inventors: Bruno Bret, Colmar; Jean-Francois Leboeuf, Horbourgwihr, both of France

[73] Assignee: Fort James France, Kunheim, France

[21] Appl. No.: 09/125,386

[22] PCT Filed: Feb. 10, 1997

[86] PCT No.: PCT/FR97/00256

§ 371 Date: Sep. 10, 1998

§ 102(e) Date: Sep. 10, 1998

[87] PCT Pub. No.: WO97/30217

PCT Pub. Date: Aug. 21, 1997

[30] Foreign Application Priority Data

Feb. 19, 1996 [FR] France ................................. 96 02023

[51] Int. Cl.[7] ............................. A61K 7/00; A61K 31/14; B32B 5/00
[52] U.S. Cl. ............................. 424/401; 424/400; 442/59; 514/642; 514/844; 514/847
[58] Field of Search ..................... 424/400, 401; 514/844, 847, 642; 442/59

[56] References Cited

U.S. PATENT DOCUMENTS

| | | | |
|---|---|---|---|
| 2,944,931 | 7/1960 | Yang et al. | 162/179 |
| 4,481,243 | 11/1984 | Allen | 428/154 |
| 5,279,767 | 1/1994 | Phan et al. | 252/357 |
| 5,415,737 | 5/1995 | Phan et al. | 162/11 |

*Primary Examiner*—Shelley A. Dodson
*Attorney, Agent, or Firm*—Breiner & Breiner

[57] ABSTRACT

The invention concerns a composition for a softening lotion which is liquid at a temperature of at least 5° C. and which is meant/to be used in treating an absorbent paper product. In the invention, this composition comprises: (a) from 1 to 10% by wt. of a component essentially containing a quaternary ammonium compound; (b) from 5 to 99% by wt. of an aqueous emollient component which contains, as active substances: (i) one or more saturated linear fatty alcohols having at least 16 carbon atoms, (ii) one or more waxy esters having a total of at least 24 carbon atoms and, where called for, (iii) one or more nonionic and/or amphoteric emulsifiers; and (c) a balance to 100% by wt. of the required amount of a solvent of the type polyol, mineral oil or their mixtures. The invention relates to the manufacture of absorbent paper products.

20 Claims, No Drawings

SOFTENING LOTION COMPOSITION, USE THEREOF IN PAPER MAKING, AND RESULTING PAPER PRODUCT

The invention concerns overall a novel composition for a softening lotion used in treating an absorbent paper product, such as a sheet of wadding cotton or tissue paper. This lotion is applied or impregnated onto at least one surface of the paper product and imparts a soft, slippery feel to the paper while being dry, i.e, without being greasy or oily. The invention also relates to the absorbent paper products wherein at least one surface is impregnated with such a lotion.

The invention is applicable to the manufacture of paper products such as domestic or sanitary papers. Among these in particular are papers entailing direct contact with the skin and repeated rubbing against the skin, for example disposable paper handkerchiefs, toilet paper or any other paper products for wiping the skin, for removing make-up, dry linen, and the like.

People afflicted with colds, influenza or various allergies causing nasal flow will wipe their noses frequently. Oftentimes such people's noses are irritated and red because of skin hypersensitization from this nasal flow. For practical reasons such people use conventional paper handkerchiefs available commercially in the form of boxed handkerchiefs, also called "facial" tissue, or folded handkerchiefs in small cases. Following several sequential nose wipings with these handkerchiefs, the skin at and around the nose becomes increasingly irritated, even inflamed and painful. Consequently, the surface of these handkerchiefs must be softened in order to limit, even suppress, any irritation caused by rubbing the handkerchief surface against the skin. Ideally the feeling should be the softness offered by a cloth handkerchief that has just been washed and pressed.

In another field, namely that of toilet paper, the same softness is required for repeated contacts with the skin taking place with simultaneous rubbing. In particular as concerns persons suffering from skin irritation in the anal region or in the case of hemorrhoids, a toilet paper with a somewhat rough feel will only further irritate the skin when this paper is pressed against this skin.

Accordingly, endeavors have been underway to generally soften the paper sheets or products such as the tissue paper webs using a variety of mechanical or chemical means.

As regards the mechanical means, techniques have been developed to improve in particular the appearance and the surface condition of the paper sheet by endowing it with a more slippery feel. In the case of handkerchiefs, illustratively, the sheet is calendered to flatten the crests formed when creping the sheet. Also the sheet surface may be frictionally treated in order to eliminate all roughnesses. However, these approaches often are insufficient. European Patent No. 0 029 269 describes a particular manufacturing procedure for such a sheet wherein the nature of the suspensions of fibers forming the various sheet layers as well as the combination of these layers among each other are significant factors for the desired velvety feel. However, this procedure limits the selection of appropriate fibers and entails constraints in the first stages of the wet process phase.

The expression "chemical means" covers any softening composition based on one or several chemical compounds. A distinction may be made between two categories of softening compositions. On one hand, the softening additives or compositions which are directly incorporated into the manufacturing pulp or composition or else are applied to a wet web of paper. And on the other hand, the softening compositions or lotions which are applied to the surface of a product or a sheet of paper in the dry state, i.e., where previous drying took place.

In the first case, these additives as a rule are used as fiber debonding agents and thereby the sheet so made is allowed to flexibilize. Many patents have been filed in this field, illustratively, EP-A-0 049 924; EP-B-0 347 176; U.S. Pat. No. 2,944,931; U.S. Pat. No. 5,415,737 and International Application No. WO 95/10661.

EP-A-0 049 924 discloses the incorporation of a quaternary ammonium compound and at least one nonionic surfactant selected from the fatty acid and the fatty alcohol ethylene oxide derivatives into the manufacturing composition in order to achieve a soft absorbent paper. The object of EP-B-0 347 176 is a tissue paper comprising at least one non-cationic surfactant applied to a wet web of paper. However, the surfactant can migrate into the sheet inside and wholly clad the fibers, thereby debonding them and decreasing tensile strength. U.S. Pat. No. 2,944,931 discloses a process for improving the softness of toilet paper and its feel consisting in adding a stable aqueous emulsion containing from 1 to 90 wt. % lanolin and from 10 to 99 wt. % of a cationic emulsifier, such as quaternary ammonium salts, to the manufacturing composition. U.S. Pat. No. 5,415,737 concerns a finished soft paper product comprising a vegetal oil-based quaternary ammonium ester compound which is also added to the manufacturing composition. International Application No. WO 95/10661 discloses a manufacturing process for a soft paper with improved feel consisting in added fatty acid ester salts of quaternary amine triethanol as softeners in the fiber aqueous suspensions. However, on the whole as regards these patents, the product or web surface does not offer the desired slippery feature. It is only the product or the web as a whole which is more soft. Moreover, the losses of softening composition during the sheet manufacturing process are more than trivial.

In the same vein, U.S. Pat. No. 5,279,767 describes more specifically a softening composition comprising a mixture of a quaternary ammonium compound and a polyhydroxy compound. This composition is prepared by mixing in a first stage these two compounds at a high temperature at which they are miscible, then in diluting the mixture in high temperature water in order to form an aqueous dispersion of vesicles (or micelles). This composition is preferably incorporated into the manufacturing composition and might be applied to the surface of the formed web, when wet, before drying. It is felt in this patent that the vesicles break up at the time of drying. Most of the polyhydroxy compound so "released" penetrates into the interior of the cellulose fibers and improves the fiber flexibility, while the other part is retained at the fiber surface and increases the absorbency rate of fibers. Because of the ionic bonds, the quaternary ammonium compound remains at the surface of the cellulose fibers and thereby the product softness and feel can be improved. This patent does not mention a slippery feel in spite of improved softness. This type of compound addresses an increase in fiber flexibility and it acts substantially within the internal sheet structure, not directly and mainly at the sheet surface. Variations of this composition are described in other patent documents such as International Application Nos. WO 94/29,520 and WO 94/29,521.

In the second case, the softening compositions are meant to be applied directly to the product surface or to the absorbent paper sheet surface that was previously dried. Their main function is as a skin emollient.

Many patents illustrate this kind of lotion.

Illustratively, with respect to toilet paper or paper towels used in proctology, U.S. Pat. No. 3,264,188 and also French Patent No. 2,376,650 describe lotions providing a fatty feel. The latter patent describes a skin wiping paper product treated with a lipophilic and cleaning emollient, the composition being substantially non-polar and non-aqueous. This emollient can be a mineral oil, petrolatum, paraffin waxes, fatty acids, fatty alcohols, fatty acid esters, derivatives of glycerides, lanolin, polysiloxanes, and the like. The emollient settles on the skin surface where it forms a thin film. It allows cleaning the skin by removing soil. Furthermore, U.S. Pat. No. 4,481,243 has as its object a two ply sheet. An emollient which provides a fatty feel is spread over a large part of the sheet surface. However, the emollient is not applied in a zone where the plies are combined by embossing.

Silicone oils, such as polysiloxanes, can be applied to a tissue paper web in the manner disclosed in European Patent Nos. 0 347 153 and 0 595 994 and in European Patent Application No. 0 656 971. However, some silicone oils are hydrophobic and lower the wettability at the surface of the paper so treated.

The object of U.S. Pat. No. 3,305,392 is a sheet of paper having an emollient applied to its surface by displacing the sheet over a comparatively solid block of an emollient composition similar to wax. This composition comprises a lubricating and softening portion such as zinc stearate; aluminum-, sodium-, calcium- or magnesium-stearate; stearic acid; esters of palmitic or spermacetic acid; stearic alcohol; and where called for additionally esters of stearic and lauric acid polyethylene glycol as effective lubricants. Compounds such as oleic acid, mineral oil, tallow glyceride, distearyl methylamine, primary and secondary fatty amines and derivatives of lanolin allowing the composition to assume a plastic shape can also be added. In order to reduce the migration of the compounds inside the sheet, agents can also be provided that contain an active group affixing itself on the cellulose fibers, these agents being cationic. Because this kind of composition is in a fairly solid state, it can be used only at lower speeds and the applied quantities will not be optimized by such techniques.

There are other patents which also relate to lotions which at ambient temperature are solid or semi-solid. U.S. Pat. No. 3,896,807 describes an emollient composition in the form of a non-adhesive and non-oily solid. This composition is heated or admixed with non-aqueous solvents of the type such as acetone, chloroform, trichloroethylene, xylene, xylol and other aromatic solvents in order to be impregnated in liquid form onto a substrate, for example, made of paper. Accordingly, this composition requires for application either heating means or solvents which for the most part for toxicologic reasons cannot be used. The main components of this composition are an oil phase containing an oil material such as mineral oil, petrolatum, paraffin, vegetal oil and different animal oils, and possibly emollients such as cetyl alcohol, propylene glycol, glycerin, triethylene glycol, waxes, and an emulsifier. This kind of lotion is significant because when moisture makes contact with the skin, this composition forms an oil emulsion in water to act as an emollient.

A more recent International Patent Application, namely WO 95/16824, furthermore suggests an anhydrous lotion which is solid or semi-solid at 20° C. but which entails constraints regarding its application to the sheet. This procedure assumes heating means and all the entailing problems both with respect to the material selected for impregnation and the liquid and stable state of the lotion which in this procedure must remain at a fairly constant temperature.

Some emollients, such as lanolin, incur drawbacks linked to their odor or to the fact they decrease the sheet absorption. European Patent No. 0 365 726 attempts to remedy these problems by proposing lotions with a single water-soluble component, namely lauroampho-glycinate, quaternary ammonium homo- or co-polymeric derivatives, a triguaternary phospholipidic complex or a glutamate glucose complex.

French Patent No. 2,538,238 describes a process in which a substrate, for example, a strip of paper from which paper towels will be made, passes through a lotion dissolved in an organic solvent and then this solvent is made to evaporate. The substrate furthermore can be impregnated practically up to saturation with an aqueous emulsion of which the ingredients are absorbed by the substrate and then dried to completely eliminate the water from the emulsion. The lotion contains a surfactant compound and a fatty body. The two above mentioned procedures entail subsequent evaporation or drying stages that preferably are avoided when manufacturing tissue paper webs.

Once applied, some lotions will alter the physical and mechanical properties of such sheets of paper, for example absorbency, tensile strength both in the direction of advance and in the transverse direction, and the like. It is especially important with respect to a lotion-impregnated sheet to retain strength properties as good as found in the same sheet if no lotion had been applied to it.

The object of the present invention is to palliate the set of drawbacks met with when using lotions applied to an absorbent paper product both when applying the lotion to a product surface and when the product is used in various ways of wiping the skin.

The object of the invention is to provide a composition for a lotion that provides an especially soft and slippery feel to the paper, thereby limiting the irritation following rubbing the paper against the skin. Other objects of the invention are to provide a composition imparting to the paper a more velvety feel and greater flexibility. Moreover, this feel remains dry, contrary to the case of some lotions which once impregnated onto a paper product leave behind a fatty feel because a film of fat is deposited on the skin or on spectacles occasionally wiped with this kind of product, handkerchief or facial tissue.

The object of the invention is to provide a lotion composition which is liquid at a temperature of at least 5° C. Preferably, the composition is liquid at a temperature from about 10 to about 40° C. thereby eliminating any difficulty in applying lotions which are solid or semi-solid at ambient temperature and, in general, requiring heating for application to the surface of a product or a sheet.

Another object of the invention is to apply a lotion in small amounts to the surface of paper products.

Another object of the invention is to provide a paper product of which at least one surface has been impregnated with such a lotion, and all consequential paper products.

The physical and mechanical properties of the absorbent paper product thus treated are not significantly modified both as regards its thickness and its absorbency and its tensile strength in the direction of advance or in the transverse direction. A product treated with the lotion can be advantageously embossed without thereby incurring any problem.

In the following description, the expression "absorbent paper product" means a sheet substantially containing paper fibers and meant for the manufacture of paper products for domestic and sanitary uses or the finished absorbent paper as such. This sheet of paper may be a tissue paper web or wadded fabric, a sheet of absorbent paper of low surface specific weight for example manufactured using a through-drying procedure, a sheet or fleece formed in the dry way and consisting of paper fibers linked by a thermoplastic binder such as a latex, or also an absorbent paper sheet constituted mostly of paper fibers and of synthetic fibers or any other equivalent paper product. The sheet can be creped or not and calendered or not. The sheet is formed by one or several plies. Other features in particular relating to the specific surface weight are elucidated in the description below.

An object of the invention is a softening lotion which is liquid at a temperature of at least 5° C. and is suitable for treating an absorbent paper product.

In an essential feature of the invention, the composition comprises:
(a) from 1 to 10 wt. % of a component substantially containing a quaternary ammonium compound;
(b) from 5 to 99 wt. % of an aqueous emollient component containing, as the active substances:
  (i) one or more linear, saturated fatty alcohols having at least 16 carbon atoms,
  (ii) one or more waxy esters having at least a total of 24 carbon atoms, and where appropriate
  (iii) one or more nonionic and/or amphoteric emulsifiers; and
(c) a balance to 100 wt. % of a sufficient amount of a solvent of the type such as polyol, mineral oil or their mixtures.

In another feature of the invention, the above aqueous component is an aqueous dispersion.

In an advantageous feature of the invention, the above aqueous emollient component comprises 15 to 45 wt. % of active substances and 55 to 85 wt. % water and, preferably, 20 to 40 wt. % of active substances and 60 to 80 wt. % water.

In still another feature of the invention, the above aqueous emollient component comprises in wt. % the following active substances:
(i) 35 to 90% saturated linear fatty acids with 18 to 24 carbon atoms,
(ii) 1 to 50% of waxy esters with a total of 24 to 48 carbon atoms,
(iii) 0 to 20% nonionic and/or amphoteric emulsifiers, and
(iv) 0 to 50% wax or mineral oil.
The total of the above quantities being about 100% by wt. of the active substances.

In a preferred feature of the invention, the composition comprises:
(a) 1 to 6 wt. % of the component containing mainly a quaternary ammonium compound,
(b) 10 to 60 wt. % of the aqueous emollient component, and
(c) a balance to 100 wt. % of the amount required as solvent.

In another preferred feature of the invention, the above quaternary ammonium compound is a salt of the following formula (I):

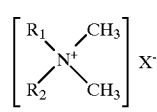

(I)

where $R_1$ is an aliphatic group, preferably with 12 to 18 carbon atoms; $R_2$ is an aliphatic group, preferably with 12 to 18 carbon atoms or an aryl group, preferably benzyl; and X is a chlorine-type halogen.

Another object of the invention is the use of a softening lotion of which the composition is defined above for treating an absorbent paper product.

In an essential feature of the invention, a quantity of about 0.30 to about 20 wt. %, referring to the dry weight of the product, of the lotion with the above defined composition is applied to the product.

In this manner, a slight emollient film is deposited and is partly fixed onto the surface of the product, whereby this product is made soft and slippery when in contact with skin.

Another object of the invention is an absorbent paper product.

In an essential feature of the invention, at least one surface of the product is impregnated with a lotion of the above defined composition.

In an another essential feature of the invention, at least one surface of the product is impregnated with a lotion and this product comprises:
paper fibers,
at least one quaternary ammonium compound,
at least one saturated linear fatty alcohol having at least 16 carbon atoms, and
at least one waxy ester having at least 24 carbon atoms.

In an advantageous feature of the invention, this product is a disposable paper handkerchief.

Other features and advantages of the invention are elucidated in the following description.

The compounds used in preparing the lotion are as follows:

The component (a) essentially contains a quaternary ammonium compound.

The quaternary ammonium compound also includes quaternary ammonium salts such as quaternary ammonium ester salts.

The quaternary ammonium salts assume the following formula (I):

(I)

where $R_1$ is an aliphatic group preferably with 12 to 18 carbon atoms; $R_2$ is an aliphatic group, preferably with 12 to 18 carbon atoms or an aryl group, preferably benzyl; and X is a chlorine-type halogen. One example of such a salt is a dimethyl ditallow quaternary ammonium chloride and, more specifically, the form wherein the tallow-alkyl group is hydrogenated. Illustratively, this can be the compound marketed as ARQUAD 2HT-75 by Akzo Chemie. At 25° C., this compound is pasty. Furthermore, a quaternary ammonium salt can be used which meets the above definition and which is liquid at 25° C. If, for a quaternary ammonium compound, the terms $R_1$ and $R_2$ in the above formula represent aliphatic groups having preferably 12 to 18 carbon atoms, then the component (a) can only contain this compound, alone or mixed with slight amounts of propanol. Also, the component (a) can contain a quaternary ammonium compound deemed essential and mixed with an ethoxylated fatty alcohol. An illustration of this mixture includes a chloride of alkyl benzyl dimethyl ammonium and an ethoxylated fatty alcohol.

The quaternary ammonium ester salts have the following formula (II):

$$\left[ \begin{array}{c} R_3 \\ \diagdown \\ N^+ \\ \diagup \\ R_4 \quad R_5 \end{array} \diagup \begin{array}{c} O \\ \| \\ R'O-C-R'' \end{array} \right] X^-$$
(II)

where R' is an alkyl group having 1 to 6 carbon atoms;

R" is an alkyl group having 12 to 18 carbon atoms;

$R_3$ is an alkyl group having 1 to 6 carbon atoms, preferably methyl;

$R_4$ is an alkyl group having 1 to 6 carbon atoms, a hydroxyl alkyl group having 1 to 6 carbon atoms, or a $$R'-O-\overset{O}{\underset{\|}{C}}-R''$$

group;

$R_5$ is alkyl group having 1 to 6 carbon atoms, a hydroxyl alkyl group having 1 to 6 carbon atoms, or a $$R'-O-\overset{O}{\underset{\|}{C}}-R''$$

group;

$X^-$ is an anion such as a chlorine-type halogen or methyl sulfate.

Advantageously some of these compounds are biodegradable.

Illustratively, a salt of the above formula (II) is referred to, wherein R' is an ethylene radical, R" is a alkyl group having 16 to 18 carbon atoms of the tallow type, $R_3$ is a methyl group, $R_4$ is a OH—$CH_2$—$CH_2$ group, $R_5$ is a $$R'-O-\overset{O}{\underset{\|}{C}}-R''$$

group, wherein R' and R" are defined above and $X^-$ is a methyl sulfate.

This compound also is called methyl triethanol ammonium sulfate dialkylester.

Other quaternary ammonium ester salts of formula (II) above can be prepared from fatty acids such as palmitic and stearic acids.

The component (a) may contain one or more compounds, quaternary ammonium ester salts, alone or mixed with a fatty alcohol and/or a solvent of the dipropylene glycol type.

The component (a) is a cationic agent. When the lotion is applied to the product or to a sheet, then in the final lotion composition, this agent serves to affix itself by means of the positive charges of the quaternary ammonium on the fibers of the sheet, in particular on the fibers at the surface of the sheet. Thereby, the other lotion components are "held back" at the surface of the sheet. The cationic compounds of the quaternary ammonium type when used in appropriate amounts also serve to flexibilize the product or sheet.

The aqueous emollient component (b) per se is of the following composition. It is noted that each of the essential constituents of the component are naturally emollient.

The component (i) comprises one or more saturated linear fatty alcohols having at least 16 carbon atoms. In general, the component (i) is a mixture of fatty alcohols of which the largest fraction (exceeding 50% by wt.) evinces chain lengths exceeding 16 carbon atoms. Therefore, most of the fatty alcohols evince a chain length above 16 carbon atoms while a small fraction of fatty alcohols is below that number. More specifically, the component (a) is a mixture of fatty alcohols with 16 to 28 carbon atoms, preferably 18 to 24 carbon atoms. Still more preferred, these saturated linear fatty alcohols have 22 to 24 carbon atoms. Examples of fatty alcohols are cetyl alcohol, stearyl alcohol, arachyl alcohol, behenic alcohol, lignoceric alcohol and ceryl alcohol. Preferably the component (i) contains behenic alcohol. The fatty alcohols are selected as natural, vegetal or animal, and as a result the aqueous emollient (b) can be biodegradable. Illustratively, the fatty alcohols are prepared from vegetal oil by transesterification, distillation, hydrogenation of the obtained esters and by fractionating crude fatty alcohols in the runoff mode. These fatty alcohols are qualified as industrial.

The length of the carbon chain of the fatty alcohol is essential to the lotion as regards its application to the surface of the paper products. A sufficiently long chain allows this kind of molecule to remain at the surface of the paper product, for example a sheet of paper, and will not penetrate the inside of the product.

The component (ii) comprises one of more waxy esters with a total of at least 24 carbon atoms. Again, a mixture of waxy esters is involved of which the largest fraction has chain lengths larger than 24. Preferably the waxy esters contain a total of 24 to 48 carbon atoms and are saturated and linear. Even more preferred, the waxy esters have a total of at least 28 carbon atoms. Ester saturation allows limiting the odor problems relating to some ester compounds. The waxy esters can be natural or synthetic.

The waxy esters are derived from saturated linear fatty acids with 6 to 24, preferably 10 to 24 carbon atoms, and more prefereably 12 to 22 carbon atoms, and of saturated linear fatty alcohols with 6 to 24, preferably 10 to 24 carbon atoms, and more preferably 12 to 22 carbon atoms.

These waxy esters therefore can be prepared from a long-chain fatty acid with a fatty alcohol of a shorter chain, or vice-versa. The chain lengths of the alcohol and the fatty acid furthermore can be identical provided that the ester has at least 24 carbon atoms. Preferably, these esters are obtained from a fatty acid and a fatty alcohol of similar and relatively long chain lengths, that is higher than 14.

Examples of waxy esters are the esters of the lauric, myristic, palmitic, stearic, arachidic and behenic acids with the lauric, myristic, cetyl, stearyl, arachyl and behenic alcohols. Illustratively, they can be decyl stearate, stearyl laurate and behenyl behenilate. Preferably cetyl stearate is used.

The component (iii) comprises one or more emulsifiers which allow the formation of a dispersion of the components (i) and (ii) in water.

Preferably, the component (iii) consists of one or more nonionic and/or amphoteric emulsifiers. These are combinations of nonionic and/or amphoteric surfactants which are distinguished by an alkylaryl, alkylene, alkyl, linear, lipophilic part and at least one hydrophilic group. This hydrophilic function can be just as well an ionic group as a nonionic group.

The nonionic emulsifiers contain hydrophilic groups, such as a polyol group, a polyalkylene glycol ether group or a combination of polyols and polyglycol ether groups.

Preferably oil-in-water (o/w) type emulsifiers are used that contain at least one of the compounds selected from a group consisting of:

(c1) linear C8–C24 alcohol derivatives, C12–C22 fatty acids, alkyl C8–C15 phenols or alkyl polyols, with 2 to 50 moles of ethylene oxide and/or 0 to 5 moles of propylene oxide, (c2) C6 to C22 unsaturated or saturated fatty acid mono- or di-esters and ethoxylated or not sorbitol or glycerol mono- or di-esters, (c3) C8–C22 alkyl mono- and oligo-glucoside or their ethoxylated analogues, (c4) ricinus oil and ricinus oil hydrogenated with 15 to 60 moles of ethylene oxide, (c5) polyols, in particular polyglycerol ester such as polyglycerol polyricinoleate or polyglycerol poly-12-hydroxystearate, and/or mixtures of these compounds.

The amphoteric emulsifiers are of the betaine type, such as the derivatives of C2 to C18 aminated acid or imidazoline derivatives.

Derivatives of the following compounds can be used as the amphoteric emulsifiers:

N-alkyl-N,N-dimethyl glycinate of ammonium, for instance ammonium dimethyl glycinate of copra fatty acid;

ammonium N-acyl-aminopropyl-N,N-dimethylglycinate;

2-alkyl-3-carboxymethyl-3-hydroxyethylimidazoline wherein the alkyl chain comprises 8 to 18 carbon atoms; and cocoasacyl-aminoethylhydroxyethylcarboxymethylglycinate.

In particular, the derivatives of fatty acid amides known as CFTA cocoamidopropylbetaine can be used.

Amphoteric emulsifiers derived from a C8–C18 or acyl alkyl group can be used of which the molecule contains at least one free amine group and a functional —COOH— or —SO$_3$H—, for example C2–C18 aminated acid derivatives such as N-alkylglycin, N-alkylaminopropionate, N-alkylsarcosinate and N-alkyliminodipropionate are preferred.

Amphoteric emulsifiers such as N-cocoalkyl-aminopropionates, cocacylaminopropionates and acylsarcosinates in C12–C18 are preferred.

The component (iii) is optional if a dispersion of components (i) and (iii) in water is desired to be carried out by mechanical means.

The fatty alcohols, waxy esters and emulsifiers are selected in such a manner that they will not raise odor problems in the lotion composition.

Other secondary emollient components (fatty acids and short chain esters, etc.) can be considered also, provided they do not alter the properties of the aqueous emollient component.

The aqueous emollient component (b) comprises, by wt. of active substances, 35 to 90% component (i), 1 to 50% component (ii), 0 to 20% component (iii) and 0 to 50% wax or mineral oil (iv), the sum of the components (i), (ii) (iii) and (iv) amounting to about 100%. Preferably, from 1 to 7 and especially from 1.5 to 5% by wt. of active substance of emulsifier (iii) is used.

The emollient component (b) of the lotion is aqueous in the form of a suspension or dispersion. Preferably it is in the form of a dispersion. The expression "dispersion" is construed broadly to mean a mixture of a liquid or solid phase in the form of globules or particles in another liquid phase serving as vehicle. The emollient component comprises 1 to 50% by wt. of active substances. More specifically, it comprises about 15 to about 45% by wt. active substances and about 55 to 85% by wt. water, and preferably about 20 to about 40% by wt. active substances and about 60 to about 80% by wt. water. Part of the water can be replaced by a mineral origin wax or oil, such as paraffin wax or oil. The concentration of the mineral-origin wax or oil (iv) in the aqueous emollient component then is about 1 to 10% by wt. of active substances. An emollient component containing only a little water is preferred for treating absorbent paper products.

Whatever the composition of the emollient component (b) defined in the above discussion, its state will be liquid at a temperature of at least 5° C. Preferably, the emollient component is liquid at ambient temperature, that is between about 10° C. and about 40° C.

The aqueous emollient component is biodegradable.

The aqueous dispersion is prepared in a vat fitted with a mixer, a cooling system and a heat exchanger. The mixture so prepared moves into a homogenizer. The dispersion is chemically and physically stable. It is homogeneous. It does not separate and practically does not thicken. The dispersion is an emollient for the skin. A compound of the fatty acid alkyl ester type is known per se to evince the function of lubricating the skin and to avert evaporative losses of skin moisture so as to preclude any skin drying. A compound of fatty alcohol type is known per se to evince the function of softening and smoothing the skin surface.

More specific illustrations concerning the aqueous emollient component are listed below.

| Component 1 | Component 2 |
|---|---|
| (a) C18–C24 saturated linear fatty alcohols | (a) C18–C22 saturated linear fatty alcohols |
| (b) C32 saturated linear waxy esters | (b) C28 saturated linear waxy esters |
| (c) emulsifier: ethoxylated fatty alcohols | (c) emulsifier: ethoxylated fatty alcohols |

Component (c) is a solvent of the polyol, mineral oil type or their mixtures. The term "polyol" herein means, for example, propylene glycol, dipropylene glycol or any equivalent compound. The mineral oil is a white vaseline oil type such as the mineral oils marketed as MARCOL or PRIMOL by Esso Corp.

Where called for, other secondary additives can be added to the lotion composition. These are conventional agents for lotions, creams or any emollient products. Among these are, for example, thickeners, perfumes, vegetal extracts, menthol, eucalyptus, niaouli and also virucidal, bactericidal compounds and the like. These agents are added in appropriate quantities to the lotion.

Components with soothing or cicatrizant properties relating to skin irritations, in particular of the nose, may be incorporated into the lotion. Known examples of such components are allantoin and some vegetal extracts.

The lotion is prepared by mixing the components (a), (b) and (c) in the presence of agitation.

The lotion composition will be, when all three constituents are present, from 1 to 10% by wt. component (a) containing essentially the quaternary ammonium compound, from 5 to 99% by wt. aqueous emollient compound (b), and a balance to 100% by wt. of the required quantity of solvent (c).

Preferably, this lotion composition comprises 1 to 6% by wt. component (a), 10 to 60% by wt. aqueous emollient component (b), and a balance to 100% by wt. of the required quantity of solvent (c).

Another lotion composition can comprise the aqueous emollient (b) and a component (c) as solvent, the components (b) and (c) then being merely mixed with component (b) being dispersed in the component, i.e., solvent (c). This kind of lotion comprises 5 to 100% by wt. aqueous emollient component (b) and a sufficient quantity for 100% by wt. of the required quantity of the component (c).

Whatever the lotion composition described above, its state will be liquid at a temperature of at least 5° C. Preferably, the composition is liquid at ambient temperature, that is approximately between 10° C. and 40° C., thereby allowing its direct application to an absorbent paper product using conventional means. Moreover, it is stable and homogeneous. Phase separation or decantation do not take place. Its viscosity is suitable to allow application in a conventional manner, namely spraying, coating or the like, onto the surface of the absorbent paper product. It can be prepared well before being applied to the product or sheet, and this latitude eliminates the need for preparation equipment at the industrial site where the lotion is applied to the product.

The lotion composition of the above formulation when applied to an absorbent paper product softens the surface of the product. The main effect of the lotion on one hand is to impart a soft and slippery feel to the paper while nevertheless remaining dry, and on the other hand to soften the surface of the skin in contact with this paper. In the illustrative case of paper handkerchiefs, the emollient and softening composition imparts a noticeably soft feel to the handkerchiefs and allows clear reduction of the irritation incurred by people who frequently wipe their noses using conventional handkerchiefs.

The discussion below elucidates the application of the lotion to paper products and in particular to a tissue paper web which is made suitable for the manufacture of paper handkerchiefs. The paper products can be treated or impregnated in part or in whole with the lotion.

The tissue paper web to be treated can be produced by any conventional manufacturing method of tissue paper. The pulps used are conventional. They can be chemical virgin pulps and/or they can be bleached in CTMP (chemical thermo-mechanical) manner. They can be from hardwood and/or coniferous sources, de-inked pulps, pulps from resinous sources or their mixtures. The manufacturing composition or aqueous fiber suspension illustratively comprises a mixture of 60% of chemically bleached conifer pulp and 40% of chemically bleached eucalyptus pulp. When using recycled fibers, the manufacturing composition comprises, for example, 50 to 95% by wt. of de-inked pulp.

The tissue paper web to be treated can be produced by any conventional manufacturing method for tissue paper. A humid resistant additive can be added in the wet phase of the sheet manufacture. The sheet can be creped or not. As regards handkerchiefs, the sheet can be calendered or not. Further, the sheet can be stratified or not. The laminae or layers may be of an identical or different fibrous and/or chemical composition. The sheet is composed of one or several plies, and preferably is of two or three plies.

A preferred manufacturing method for the handkerchiefs consists in making a handkerchief comprising three plies of a different nature or composition. The central ply's composition is fibrous and comprises mostly long fibers, for example pulps based on resin fibers, preferably from pine trees and spruces. A moisture-resistant additive is incorporated into the manufacturing composition of this ply. If this additive is already present in some amount in each of the other two plies, a large quantity shall be incorporated into the central ply. Illustratively, this additive is a moisture resistant resin of the epichlorohydrine polyamide type marketed as KYMENE SLX by Hercules Corp. The two other plies are placed one on each side of the central ply and constitute the web's surfaces. Their composition is substantially of short fibers, for example based on eucalyptus fiber-containing pulps. These plies comprise a softener or a debonder. The web so made offers very good wet strength and hence good solidity in particular on account of the central ply. This web also provides improved surface softness due to the selection of the fibrous and chemical compositions of the other two outer plies.

The specific surface weight of the sheet ranges approximately from 12 to 65 g/m². For facial tissue corresponding to the commercial boxed handkerchiefs, the specific surface weight is about 30 to 45 g/m² and for a handkerchief folded and conditioned in a small case, the specific surface weight is about 35 to 65 g/m².

The lotion is applied at least to one side of the tissue paper web in its dry state and preferably on both outer sides of the sheet. This treatment can be carried out in several stages of the sheet manufacture as soon as the sheet has been dried. On a conventional paper-making machine, this treatment can take place immediately following the sheet's drying stage on the yankee cylinder once the sheet has been creped or following the drying stage by through-drying for another manufacturing procedure. At this stage a single ply is being treated on a single side. The treatment also can take place at the re-spooling stage when several plies are combined to form the sheet. One or both external sides of the sheet are treated consecutively or simultaneously. The lotion also can be applied during the conversion phase of the sheet into a finished product, toilet paper, handkerchief, etc. In the case of handkerchief manufacture, the two sides of the sheet illustratively are treated just before the embossing stage of the edges defining a handkerchief, this stage occurring before the stage of cutting and folding the handkerchief, (an edge embossing procedure is described in French Patent No. 2,698,314), alternatively, for example, after embossing and combining the plies. The product may be embossed on only one of its sides. It may be embossed also on all or part of its surfaces. Any processing other than embossing to impart a specific pattern or appearance to the paper web also may be considered. Further, there can also be lotion treatment of the finished absorbent paper product. It has been observed with surprise that the sheet surfaces treated with and hence impregnated by the lotion no matter at what point in the manufacturing procedure or conversion of the sheet (following sheet drying) will be embossable without any difficulty. This feature is an advantage over the lotions of the prior art, in particular some lotions evincing a fat feel, that could not be applied onto paper surfaces that subsequently would be embossed and thus precluded the paper from being embossed.

The lotion is applied to the product or sheet in an amount of about 0.30 to about 20, and preferably from about 0.65 to about 15, % by wt. (weight of the aqueous composition) based on dry weight of the product (before the lotion is applied). Preferably, the lotion is applied in an amount of about 1 to about 10% by wt. of dry fibers. This amounts to applying a quantity from about 0.3 g/m² to about 3 g/m² to each surface of the product or sheet.

More preferably, and by optimizing the quantities of lotion used and the desired paper surface softness, less than 2% by wt. of active ingredient lotion relative to the dry product weight is applied. The end product so treated then includes less than 2% of active lotion ingredients relative to the dry weight of the absorbent paper.

In general, clearly improved surface softness is achieved in selecting for the lotion composition at least one waxy ester having at least a total of 24 to 48 carbon atoms and incorporating it in sufficient quantity into the composition to have at least 3% by wt. of active ingredients of this ester on the surface of dry weight of the absorbent paper product at the surface of the absorbent paper product.

The lotion can be applied in different ways, for example spraying or atomization, coating, flexographic printing or any other method allowing deposition of the lotion on the web surface.

Atomization or spraying is carried out using a system of conventional nozzles, wherein lotion droplets are projected onto an outer sheet surface. Atomization is further carried out by devices with air mixing or without air and at low pressure or using rotors. This is a simple application procedure and the sheet does not make contact with the application device. It has been observed that when the application is by atomization, and when treating the two outer surfaces of a sheet with three plies, the lotion will partly penetrate inside the sheet as far as the inner ply. When using this technique, quantities of about 1.5 to 3 $g/m^2$ are applied.

Coating is carried out using a cylinder-screen onto which the lotion is deposited. The cylinder is made to contact one side of the sheet. The two sides of the sheet can be treated simultaneously using one cylinder per side. The lotion can be deposited on all or a part of the cylinder surface, for example in the form of strips. Moreover, variable quantities of lotion can be deposited on parts of the cylinder surface and consequently as such on the side of the sheet. Using such a coating procedure, it has been noted that the lotion does not penetrate the inside of a three-ply sheet as far as the inner ply and does remain well localized on the sheet surface. As a result, it is possible to advantageously reduce the quantities of applied lotion of the invention on each side of the sheet. The quantities applied by the coating technique range from about 0.3 to about 2 $g/m^2$, and preferably from about 0.5 to about 1.5 $g/m^2$, per side. Other appropriate coating techniques also can be considered.

Tests on a prototype machine were carried out using different lotion compositions. A three-ply sheet was treated on both sides. Treatment was either by atomization from a rotor-fitted device or using a coating cylinder.

Control 0

A tissue paper web comprising three plies each of 18 $g/m^2$ was converted into cut handkerchiefs of which the edges were bonded and embossed in the manner described in French Patent No. 2,698,314.

EXAMPLE 1

A composition was used containing 100% by wt. of the aqueous emollient component corresponding to the Lotion A of which the composition is as follows:

| Lotion A (dispersion) |
| --- |
| (i) C18–C24 saturated linear fatty alcohols |
| (ii) C32 saturated linear waxy esters |
| (iii) Emulsifier: ethoxylated fatty alcohols |

This lotion was applied on a pilot machine to a tissue paper web by means of a rotor-fitted device. In the dry state, the tissue paper web to be treated comprising three plies each of 17 $g/m^2$ was calendered. The lotion was applied at the rate of 2.5 $g/m^2$ per side. The web thusly treated with the Lotion A then was converted into a handkerchief in the manner of the procedure described in French Patent No. 2,698,314.

The same web, but untreated by the lotion, also was converted into a handkerchief by the above procedure and served as Control 1.

EXAMPLE 2

The composition of Lotion A of Example 1 was applied to a calendered web comprising three plies each of 20.5 $g/m^2$. The treatment was implemented using a coating cylinder. A quantity of 0.6 $g/m^2$ was applied to each side of the sheet, the total applied quantity being comparatively small and especially advantageous. The sheet so treated with Lotion A then was converted into a handkerchief in the manner of French Patent No. 2,698,314.

The same web untreated with Lotion A also was converted into a handkerchief by the above described procedure and served as Control 2.

EXAMPLE 3

A Lotion B based on the three components (a), (b) and (c) was prepared. The composition of Lotion B was as follows:

| Lotion B | |
| --- | --- |
| | % by weight |
| (a) Dimethyl ditallow quaternary ammonium chloride (ARQUAD 2 HT-75) | 4% |
| (b) Aqueous emollient component- (i) C18–C24 saturated linear fatty alcohols (ii) C32 saturated linear waxy esters (iii) emulsifier: ethoxylated fatty alcohols | 20% |
| (c) Propylene glycol | 76% |

Lotion B was applied by a rotor-fitted device. The tissue paper web to be treated comprised three plies each of 18 $g/m^2$ and was calendered. The quantity applied to each side was 2.5 $g/m^2$. The web thusly treated with Lotion B then was converted into a handkerchief in the manner of French Patent No. 2,698,314.

The same web, but untreated with the Lotion, also was converted into a handkerchief by the above procedure and served as Control 3.

EXAMPLE 4

A Lotion C of the following composition was prepared:

| Lotion C | |
| --- | --- |
| | % by weight |
| (a) Dimethyl ditallow quaternary ammonium chloride (ARQUAD 2 HT-75) | 4% |

-continued

| Lotion C | |
|---|---|
| | % by weight |
| (b) Aqueous emollient component- | 40% |
| (i) C18–C24 saturated linear fatty alcohols | |
| (ii) C32 saturated linear waxy esters | |
| (iii) emulsifier: ethoxylated fatty alcohols | |
| (c) Propylene glycol | 56% |

This lotion was then applied to a sheet of paper by a coating cylinder. The tissue paper web to be treated comprised three plies each of 20.5 g/m² and was calendered. The applied quantity was 0.6 g/m². The sheet thusly treated with Lotion C then was converted into a handkerchief in the manner of French Patent No. 2,698,314.

The same sheet, but untreated with Lotion C, corresponds to Control 2.

EXAMPLE 5

The Lotion C composition was used to treat a sheet which was similar to that of Example 4 on a prototype coating machine. Only the amount of applied Lotion was changed. The quantity applied per side in this instance was 1.3 g/m². The sheet thusly treated with Lotion C then was converted into a handkerchief in the manner of French Patent No. 2,698,314.

The same sheet, but untreated with the Lotion, corresponds to Control 2.

The handkerchiefs made in Examples 1 through 5 and the Control handkerchiefs were sense-tested on 40 persons.

A series of tests were carried out concerning the parameters of softness, flexibility and thickness. The person testing the product selects a qualifier on a verbal scale. The method consisted in giving grades to this verbal scale as shown in the Table below by comparing on one hand one of the handkerchiefs of one of Examples 1 through 5 and on the other hand the Control handkerchief corresponding to 1 through 5 with the same Control 0 for a given parameter.

| Verbal scale/Grade | |
|---|---|
| Clearly less | −3 |
| Less | −2 |
| Probably less | −1 |
| The same | 0 |
| Probably more | +1 |
| More | +2 |
| Clearly more | +3 |

The number of persons having selected a given qualifier was multiplied by the grade of this qualifier. Then the products obtained were added and the addition divided by the total number of persons to obtain the average grade. This average grade which must be between −3 and +3 is the test result. Table I below lists the test results. Be it noted that the Controls 1 through 5 without lotion already evince a fairly high level of softness which is inherent in the particular manufacturing procedure of the tissue paper web. Accordingly, the softness of the handkerchiefs impregnated with the lotion of the invention is appreciated relative to a level which is already known as being good.

TABLE I

| | Softness | Flexibility | Thickness |
|---|---|---|---|
| Control 1 | +0.15 | −0.6 | −0.6 |
| Example 1 | +1.2 | +0.2 | −0.45 |
| Control 2 | +0.35 | −0.3 | −0.15 |
| Example 2 | +1.15 | +0.1 | −0.25 |
| Control 3 | +1 | −0.45 | −0.25 |
| Example 3 | +1.65 | −0.35 | −0.25 |
| Control 2 | +0.55 | −0.35 | −0.1 |
| Example 4 | +1.45 | −0.15 | 0 |
| Control 2 | +0.75 | −0.15 | −0.2 |
| Example 5 | +2 | +0.05 | +0.1 |

Test result significance is computed by the $X^2$ method.

The results of Example 1 and Control 1 are significant to 1% regarding flexibility and softness. The result concerning thickness of Control 1 is significant to 1% and the result concerning the thickness of Example 1 is significant to 5%.

The results for Example 3 and Control 3 are significant to 1% regarding softness.

No significance attaches to the results for flexibility and thickness concerning Examples 2, 4 and 5 and their respective Controls 2.

On the other hand for these same Examples 2, 4 and 5 and the respective Control 2, the results are significant to 1% regarding softness.

Only parameters with significant test results will be discussed. Thickness is perceived being practically unmodified.

For the case of significant results, flexibility is improved.

Lastly for almost all the significant results of Examples 1 through 5, the handkerchiefs were perceived as probably being softer (verbal scale) compared with the Control 0 which per se was already soft.

The difference between an Example and its Control allows evaluation of the effect of the lotion per se on the sheet by eliminating the influence of the sheet and of its manufacture.

The best results (difference between Example 1 and its Control) regarding softness obtained for Examples 5 and 1 respectively corresponding to the Lotion C applied by coating at a rate of 1.3 g/m² per side and to the Lotion A applied by atomization at a rate of 2.5 g/m² per side.

With respect to the quantity applied, the test results for the handkerchiefs of Examples 5, 4 and 2 (difference between the Example and its Control) that are the most significant, namely, for Examples 5 and 4, for Lotion C applied by coating at a rate of 0.6 and 1.3 g/m² per side and as regards Example 2, for Lotion A applied by coating at a rate of 0.6 g/m² per side.

A hierarchy was set up for some handkerchiefs regarding the softness parameter and the overall preference of the set of parameters softness, flexibility and thickness. The method used in this hierarchy is that of the mean rank. Table II below shows the results:

TABLE II

|  | Softness preference | Overall preference |
|---|---|---|
| Example 2 | 2.2 | 2.5 |
| Example 4 | 2.3 | 2 |
| Example 5 | 1.5 | 1.5 |

The handkerchiefs of Examples 2, 4 and 5 illustrate the coating procedure.

The handkerchief of Example 5 was clearly first in preference both regarding softness and the set of parameters.

The handkerchiefs of Examples 2 and 4 practically are even in second place with respect to softness.

The handkerchief of Example 4 is in second place for overall preference and the handkerchief of Example 2 is in third position.

Consequently, Lotion C (Examples 4 and 5) was generally preferred over Lotion A (Example 2) and more definitively when it was applied by coating at a rate of 1.3 g/m² per side.

As regards the physical and mechanical properties of the handkerchiefs thusly impregnated, the dry strengths were measured in the direction of advance (DA) and in the transverse direction (TD); the elongation measured in the direction of advance (DA); and the wet strengths in the direction of advance (DA) and in the transverse direction (TD).

The test results for Examples 4 and 5 are listed in Table III below.

TABLE III

|  | DRY STRENGTHS | | | WET STRENGTHS | |
|---|---|---|---|---|---|
|  | DA | TD | elongation DA | DA | TD |
| Example 4/Control 2 | 0% | 5% | 0% | −1% | −5% |
| Example 5/Control 2 | 0% | 0% | 0% | −8% | 3% |

The properties listed by the test results in Table III are not substantially affected. They are as good as those of the Control (a difference of 5 to 8% lacking significance for the wet strengths). This feature represents an appreciable advantage.

The absorbencies also were measured for the handkerchiefs of the set of Examples. While a significant loss in such a property was expected, in fact the losses proved slight.

Accordingly, treating the absorbent paper products with the lotion of the invention does not entail negative effects on the physical and mechanical properties of the product.

It is claimed:

1. A composition for a softening lotion which is liquid at a temperature of at least 5° C. for use in treating an absorbent paper product, the composition comprising:
   (a) from 1 to 10 wt. % of a component substantially containing a quaternary ammonium compound;
   (b) from 5 to 99 wt. % of an aqueous emollient component comprising as active substances:
      (i) at least one saturated linear fatty alcohol having at least 16 carbon atoms,
      (ii) at least one waxy ester having a total of at at least 24 carbon atoms, and optionally
      (iii) at least one nonionic emulsifier and/or amphoteric emulsifier; and
   (c) a balance to 100 wt. % of a solvent which is a polyol, mineral oil or mixtures thereof.

2. Composition as claimed in claim 1 wherein the aqueous emollient compound is an aqueous dispersion.

3. Composition as claimed in claim 1 or 2 wherein the at least one fatty alcohol of (i) has 16 to 28 carbon atoms and the at least one waxy ester of (ii) has 24 to 48 carbon atoms.

4. Composition as claimed in claim 3 wherein the at least one waxy ester of (ii) is synthetic and derived from saturated linear fatty acids having 6 to 24 carbon atoms and from saturated linear fatty alcohols having 6 to 24 carbon atoms.

5. Composition as claimed in claim 1 or 2 wherein the aqueous emollient component comprises 1 to 50 wt. % of active substances.

6. Composition as claimed in claim 5 wherein the aqueous emollient component comprises 15 to 45 wt. % of active substances and 55 to 85 wt. % water.

7. Composition as claimed in claim 6 wherein the aqueous emollient component comprises 20 to 40 wt. % of active substances and 60 to 80 wt. % water.

8. Composition as claimed in claim 1 or 2 wherein the aqueous emollient component comprises active substances by wt. as follows:
   (i) 35 to 90% of saturated linear fatty alcohols having 18 to 24 carbon atoms,
   (ii) 1 to 50% of waxy esters with a total of 24 to 48 carbon atoms,
   (iii) 0 to 20% of nonionic and/or amphoteric emulsifiers, and
   (iv) 0 to 50% of wax or mineral oil,
wherein total component amounts of the active substances amount to 100% by wt. of the aqueous emollient component.

9. Composition as claimed in claim 1 or 2 wherein the aqueous emollient component includes behenic alcohol as the fatty alcohol of (i).

10. Composition as claimed in claim 1 or 2 wherein the composition comprises:
   (a) from 1 to 6 wt. % of the component substantially containing a quaternary ammonium compound,
   (b) from 10 to 60 wt. % of the aqueous emollient component, and
   (c) a balance to 100 wt. % of the solvent.

11. Composition as claimed in claim 1 or 2 wherein the quaternary ammonium compound is a salt having a formula (I) as follows:

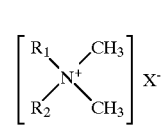

wherein $R_1$ is an aliphatic group having 12 to 18 carbon atoms; $R_2$ is an aliphatic group having 12 to 18 carbon atoms or an aryl group; and X is chlorine.

12. Composition as claimed in claim 11 wherein the quaternary ammonium compound is dimethyl ditallow quaternary ammonium chloride.

13. Composition as claimed in claim 1 or 2 wherein the component of (a) is a mixture comprising alkyl benzyl dimethyl ammonium chloride and an ethoxylated fatty alcohol.

14. Composition as claimed in claim 1 or 2 wherein the quaternary ammonium compound is a quaternary ammonium mono-, di- or tri-ester of formula (II) as follows:

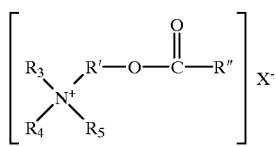 (II)

where R' is an alkyl group having 1 to 6 carbon atoms;
R" is an alkyl group having 12 to 18 carbon atoms;
$R_3$ is an alkyl group having 1 to 6 carbon atoms;
$R_4$ is an alkyl group having 1 to 6 carbon atoms, a hydroxyl alkyl group having 1 to 6 carbon atoms, or a

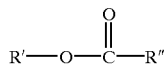

group; and $R_5$ is alkyl group having 1 to 6 carbon atoms, a hydroxyl group having 1 to 6 carbon atoms, or a

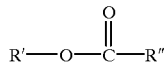

group; and

X is an anion of chlorine or methyl sulfate.

15. Composition as claimed in claim 14 wherein R' is an ethylene group, R" is an alkyl group having 16 to 18 carbon atoms, $R_3$ is a methyl group, $R_4$ is a hydroxyethylene group, $R_5$ is a

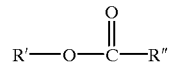

group, and X is methyl sulfate.

16. Composition as claimed in claim 1 or 2 wherein the solvent is a propylene glycol or a dipropylene glycol.

17. Method of using a softening lotion in treating an absorbent paper product comprising providing the composition of said lotion as claimed in claim 1 or 2, and applying said lotion to the paper product in an amount of about 0.30 to about 20% by wt. based on the dry weight of the product.

18. Method as claimed in claim 17 wherein the amount applied is about 1 to about 10% by wt. based on the dry weight of the product.

19. Method of claim 17 wherein said lotion is an additive for the absorbent paper product.

20. An absorbent paper product having at least one surface of said product impregnated with a lotion of the composition as claimed in claim 1 or 2.

* * * * *